(12) United States Patent
McCombs et al.

(10) Patent No.: US 6,935,460 B2
(45) Date of Patent: Aug. 30, 2005

(54) NOISE MUFFLER FOR OXYGEN CONCENTRATOR

(75) Inventors: Norman R. McCombs, Tonawanda, NY (US); Michael R. Valvo, East Aurora, NY (US)

(73) Assignee: AirSep Corporation, Buffalo, NY (US)

( * ) Notice: Subject to any disclaimer, the term of this patent is extended or adjusted under 35 U.S.C. 154(b) by 0 days.

(21) Appl. No.: 10/442,581

(22) Filed: May 21, 2003

(65) Prior Publication Data

US 2004/0231913 A1 Nov. 25, 2004

(51) Int. Cl.$^7$ .............................. F01N 1/24; F01N 1/10; B01D 35/00; B01D 46/30
(52) U.S. Cl. ..................... 181/258; 181/230; 181/222; 181/252; 181/256; 210/349; 55/498
(58) Field of Search ................................. 181/258, 230, 181/231, 268, 275, 281, 222, 252, 256, 257; 210/349; 55/498, 504, 505

(56) References Cited

U.S. PATENT DOCUMENTS

| | | | | |
|---|---|---|---|---|
| 1,326,647 A | * | 12/1919 | Cotton et al. ................ | 181/258 |
| 3,384,200 A | * | 5/1968 | Baker et al. ................. | 181/230 |
| 3,635,309 A | * | 1/1972 | Nemcansky et al. ........ | 181/267 |
| 3,949,828 A | * | 4/1976 | Frochaux ..................... | 181/230 |
| 4,082,160 A | * | 4/1978 | Schilling et al. ............ | 181/258 |
| 4,134,472 A | * | 1/1979 | Trainor ....................... | 181/258 |
| 4,314,832 A | * | 2/1982 | Fox ............................. | 55/482 |
| 4,318,720 A | * | 3/1982 | Hoggatt ...................... | 181/267 |
| 4,424,883 A | * | 1/1984 | Musiani ...................... | 181/258 |
| 4,749,058 A | * | 6/1988 | Trainor ....................... | 181/239 |
| 4,768,616 A | * | 9/1988 | Richard et al. ............. | 181/233 |
| 4,884,657 A | * | 12/1989 | Osada ......................... | 181/258 |
| 5,549,720 A | * | 8/1996 | Miller et al. ................. | 55/324 |
| 6,089,346 A | * | 7/2000 | Tredinnick et al. ......... | 181/230 |
| 6,202,785 B1 | * | 3/2001 | Hilling et al. .............. | 181/230 |
| 6,668,971 B2 | * | 12/2003 | Sterling ...................... | 181/230 |
| 6,702,880 B2 | * | 3/2004 | Roberts et al. ............. | 181/256 |
| 2004/0040274 A1 | * | 3/2004 | Amann ........................ | 55/498 |

\* cited by examiner

*Primary Examiner*—Edgardo San Martin
(74) *Attorney, Agent, or Firm*—Hiscock & Barclay, LLP

(57) ABSTRACT

A noise muffler for the exhaust of waste gases from apparatus such as an oxygen concentrator, including a muffler core with an inlet to receive the waste gases and a plurality of bores in the core first to direct the waste gases through a filter material and a cap enclosing the filter material and forming a plurality of outlets to direct the waste gases out of the muffler, the bores and outlets positioned to cause the waste gases to change their direction of flow multiple times before exiting the muffler.

13 Claims, 6 Drawing Sheets

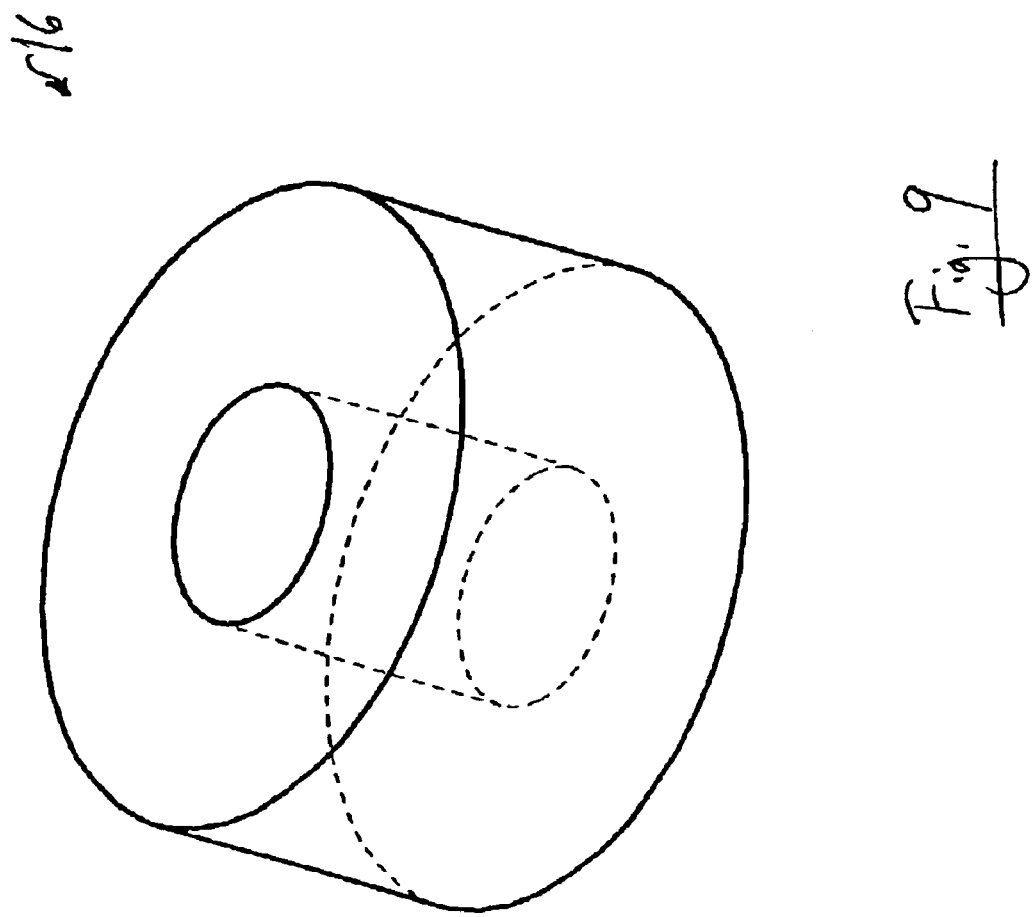

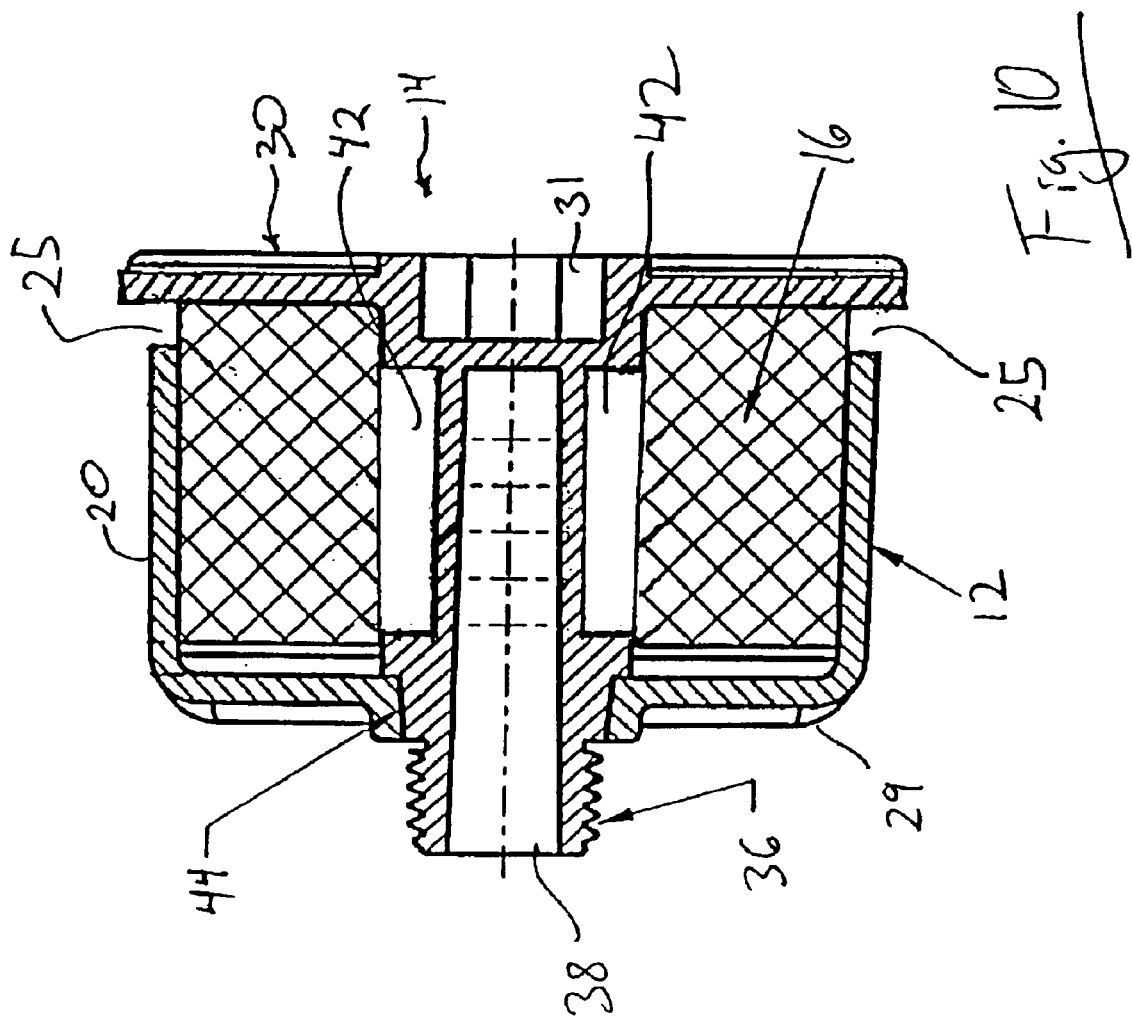

NOISE MUFFLER FOR OXYGEN CONCENTRATOR

FIELD OF THE INVENTION

This invention relates to noise mufflers for the exhaust of gas handling apparatus.

BACKGROUND OF THE INVENTION

Gas handling apparatus such as oxygen concentrators are often used in medical applications by patients that have difficulty breathing. Whether the oxygen concentrator is used by a patient in a hospital or in the home, the noise output by the oxygen concentrator is an important consideration, especially when the patient and those nearby are trying to sleep. A significant contributor to the noise made by an oxygen concentrator is the noise made by the exhaust of the oxygen concentrator. Therefore, an improved noise muffler for the exhaust of an oxygen concentrator is desired in the art. Further, oxygen concentrators are usually required to be somewhat portable to enable patient mobility. Therefore, a noise muffler having a simple, compact, and durable design is further desired in the art.

SUMMARY OF THE INVENTION

The present invention provides an improved noise muffler for the exhaust of a gas handling apparatus.

The invention comprises, in one form thereof, a substantially cylindrical core having an inner core surface, an outer core surface, an open end, and a closed end. A plurality of radial bores connects the inner core surface with the outer core surface. A flange is integral with or affixed to the closed end of the core. A filter comprising woven or non-woven polymer fibers surrounds the core and abuts the flange.

The noise muffler further includes a substantially cylindrical cap having an inner cap surface engaging the filter, a first end including a plurality of clips penetrating the flange, and a covered end opposite to the first end of the cap. The open end of the core penetrates the covered end of the cap. A plurality of outlets is formed between the first end of the cap and the flange and between the plurality of clips of the cap.

The noise muffler of the present invention provides a compact and lightweight muffler for gas handling systems and consists of a minimum number of parts.

BRIEF DESCRIPTION OF THE DRAWINGS

The above-mentioned and other features and advantages of this invention, and the manner of attaining them, will become apparent and be better understood by reference to the following description of one embodiment of the invention in conjunction with the accompanying drawings, wherein:

FIG. 9 is an isometric view of the filter of FIG. 3; and

FIG. 10 is a cross-sectional view of the noise muffler as taken on line 10—10 of FIG. 2 and rotated 45 degrees relative to the cross-sectional view of FIG. 3.

Corresponding reference characters indicate corresponding parts throughout the several views. The exemplifications set out herein illustrate the preferred embodiments of the invention and such exemplifications are not to be construed as limiting the scope of the invention in any manner.

DETAILED DESCRIPTION

Figure 1:
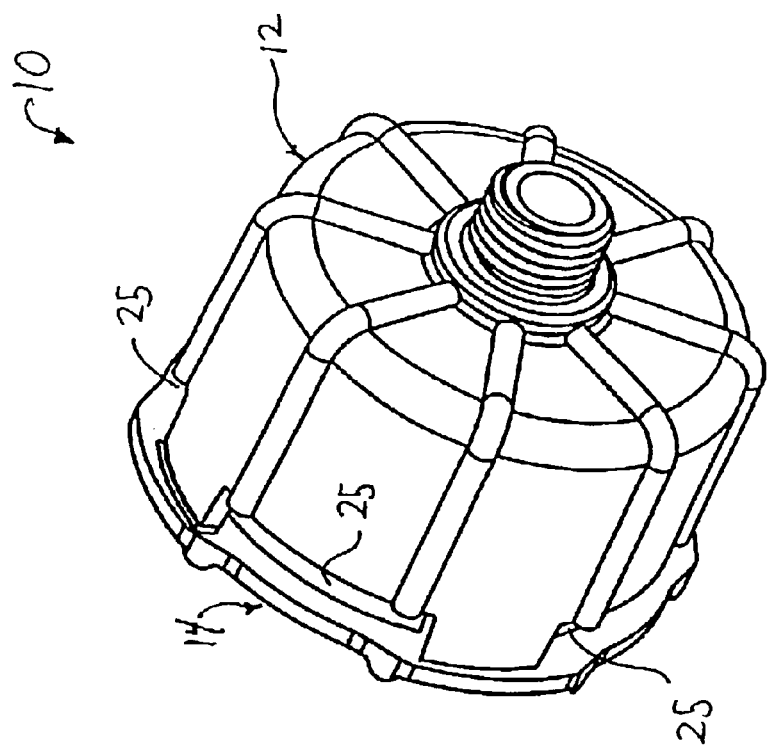
FIG. 1 is an isometric view of the noise muffler of the present invention.
Figure 2:
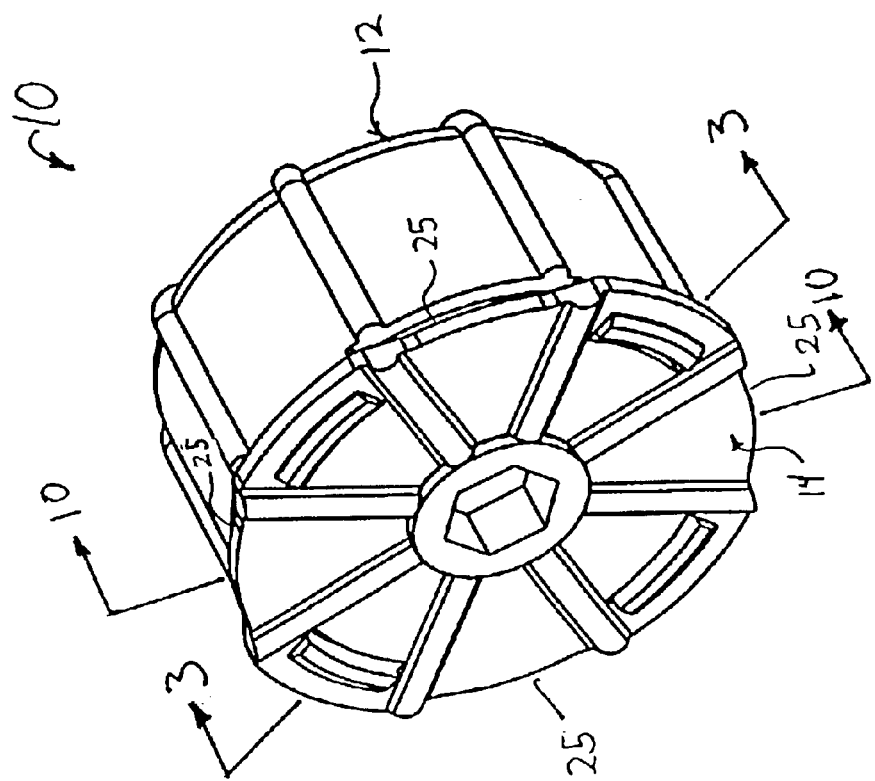
FIG. 2 is a second isometric view of the noise muffler as taken on line 3—3 of FIG. 2.

Referring to FIGS. 1 and 2, there is shown the noise muffler of the present invention. The noise muffler 10 includes a muffler cap 12, a muffler core 14, and a filter 16 shown in FIG. 3.

Figure 4:
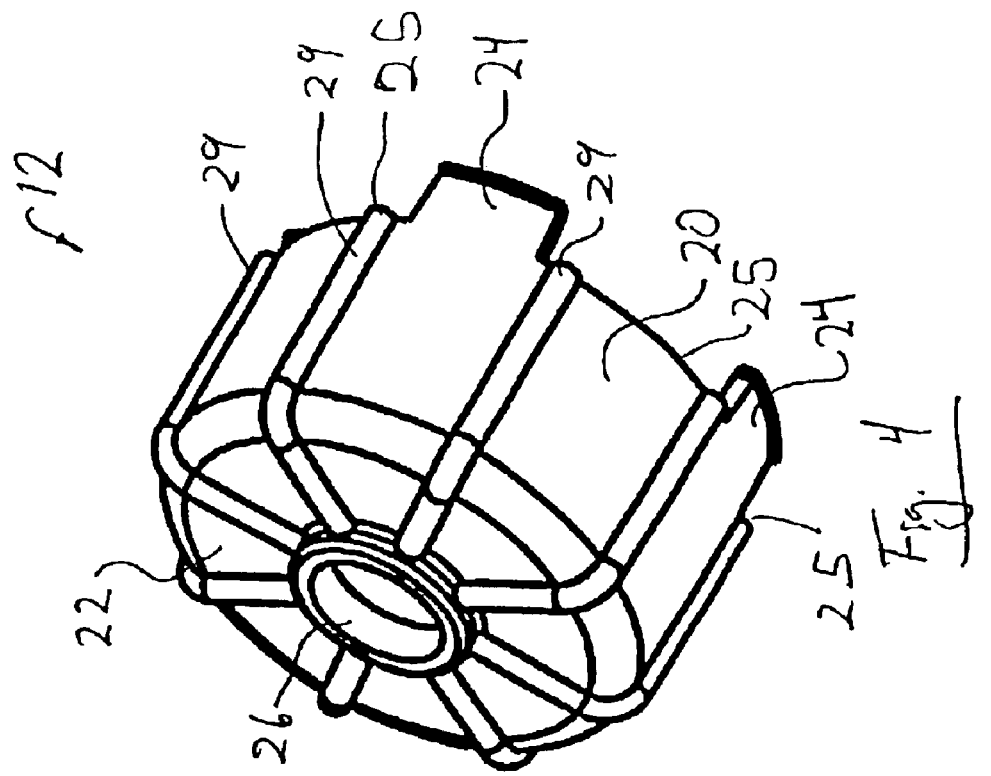
FIG. 4 is an isometric view of the muffler cap of FIG. 1.
Figure 5:
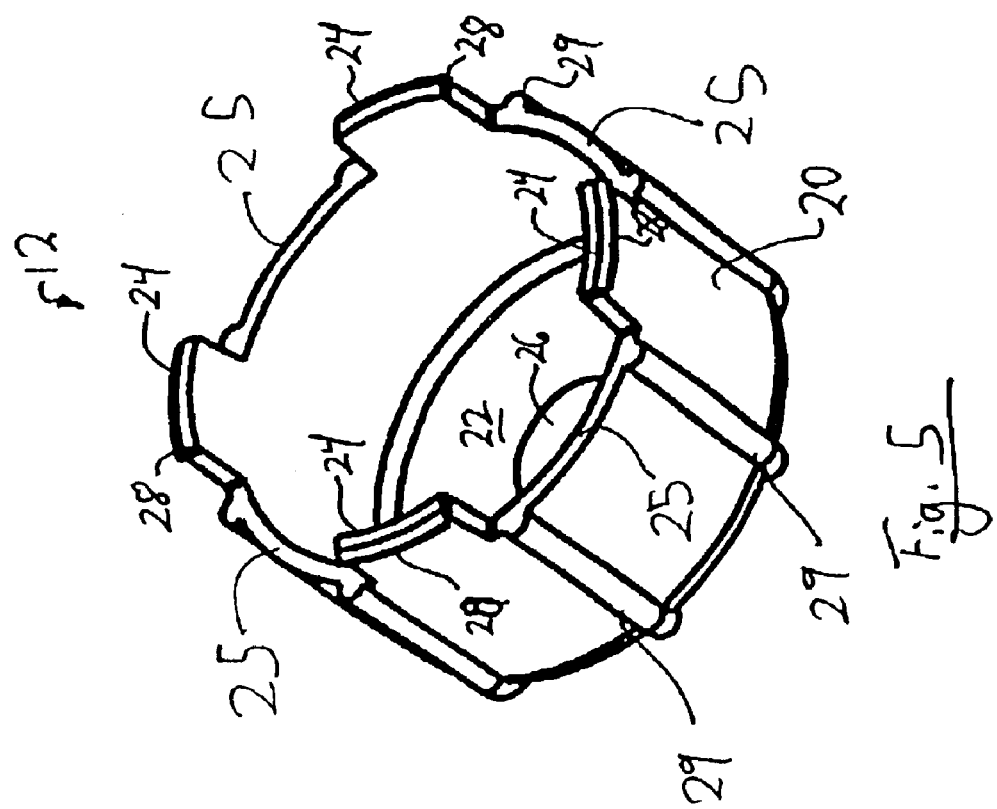
FIG. 5 is a second isometric view of the muffler cap of FIG. 4.

Referring now to FIGS. 4 and 5, muffler cap 12 includes a substantially cylindrical wall 20, a covered end 22, a plurality of clips 24, and a plurality of recesses or outlets 25. The covered end 22 is integral with or affixed to the cylindrical wall 20 and includes an axial through hole 26. The clips 24 are integral with or affixed to the cylindrical wall 20 and each clip 24 includes an outward pointing lip 28. The muffler cap 12 is shown having four clips 24, however any number of clips may be used. A plurality of ribs 29 are integral with or affixed to the outer surfaces of the cylindrical wall 20 and the covered end 22. The ribs 29 add strength to the muffler cap 12.

Figure 7:
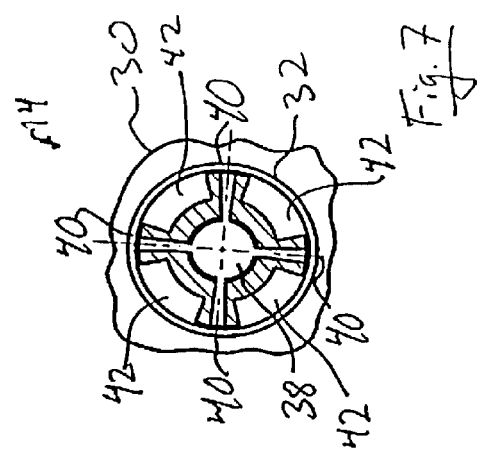
FIG. 7 is a view of section 7—7 of the muffler core of FIG. 5.
Figure 8:
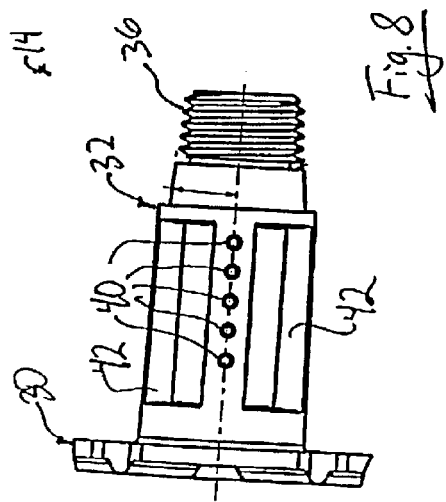
FIG. 8 is a side view of the muffler core of FIG. 5.
Figure 6:
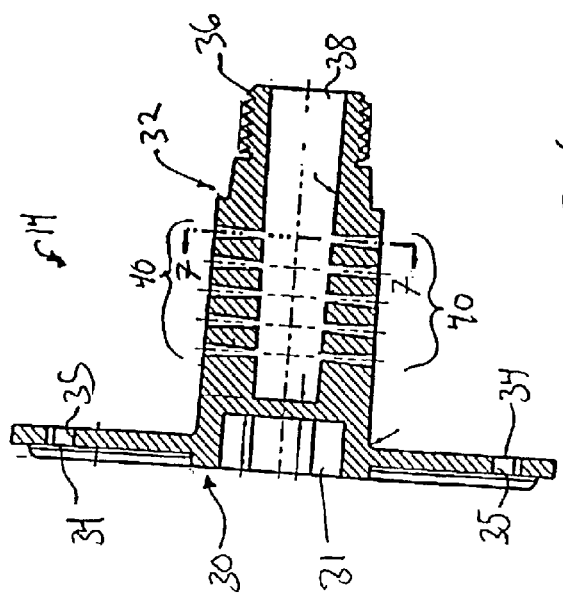
FIG. 6 is a cross-sectional view of the muffler core of FIG. 1.

Referring now to FIG. 6, the muffler core 14 includes a flange 30 and a central piece 32. The flange 30 includes a central blind bore 31 being configured for engaging a hexagonal wrench. The flange 30 further includes a plurality of slots 34 configured for engaging the clips 24. Each of the slots 34 includes an inner edge 35. The central piece 32 is integral with the center of the side of the flange 30 opposite to the central blind bore 31. The central piece 32 includes a threaded end 36, an axial blind bore 38, and a plurality of radial bores 40. The axial blind bore 38 has a decreasing diameter from the threaded end 36. Each row of radial bores has five radial bores 40 as shown in the drawings, however different applications may require a different number of radial bores 40. Further, as shown in FIG. 7, the central piece 32 includes 4 rows of radial bores 40; however, the number of rows of radial bores 40 may be different for particular applications. Each of the radial bores 40 has an increasing diameter from the axial blind bore 38. In the preferred embodiment, the size and number of the radial bores 40 provide ample flow from the axial blind bore 38 to thereby reduce any backpressure within the axial blind bore 38. As best seen in FIGS. 7 and 8, a plurality of depressions 42 are located between the rows of radial bores 40 to reduce the weight and material used in the central piece 32.

As seen in FIG. 9, the filter 16 is substantially cylindrical and includes and axial bore for engaging the central piece 32. The outer radius of the filter 16 is greater than the distance from the axis of the flange 30 to the inner edges 35 of the slots 34. The filter 16 is made of felt or a similar material comprising polymer fibers formed into a firm cloth.

Figure 3:
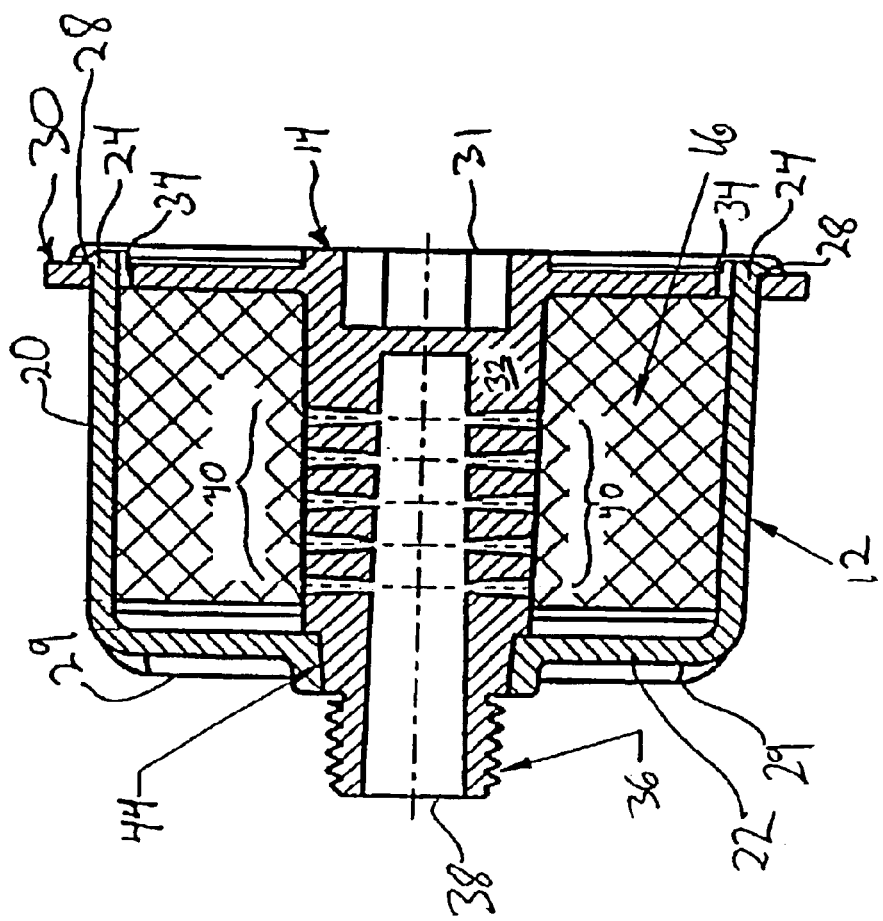
FIG. 3 is a cross-sectional view of the noise muffler of FIG. 1.

In use, the filter 16 is placed on the central piece 32 such that the inner surface of the filter 16 contacts the radial bores 40 and one end of the filter 16 abuts the flange 30. As shown in FIG. 3, the muffler cap 12 slides over the filter 16 such that the inner surface of the cylindrical wall 20 contacts the filter 16. The threaded end 36 of the central piece 32 slides through the through hole 26 of the muffler cap 12 until the clips 24 snap into the slots 34. The outward pointing lips 28 engage the outer surface of the flange 30. In the preferred embodiment, the interface 44 between the central piece 32 and the through hole 26 of the muffler cap 12 is tapered and has an interference fit of approximately 0.002-in. Referring to FIG. 1 and FIG. 10, the assembled noise muffler 10 forms outlets 25.

The threaded end 36 of the central piece 32 is threaded onto the exhaust of a gas handling apparatus such as an oxygen concentrator. A secure fit is achieved by tightening the muffler core 14 with a wrench such as a hexagonal wrench engaging the central blind bore 31 of the flange 30. The pressurized exhaust gas enters the noise muffler 10 through the axial blind bore 38 and proceeds to the radial bores 40. The gas then passes from the radial bores 40 to the filter 16. The polymer fibers of the filter 16 absorb the kinetic energy of the gas, thereby slowing it down. The gas exits the noise muffler 10 through the outlets 25 with less energy and therefore, quietly. Further, the two directional changes applied to the flow by the noise muffler 10 reduces the noise of the gas flow.

It should be particularly noted that because of the integral nature of the muffler core 14, the noise muffler 10 is comprised of only a few readily molded parts and is therefore inexpensive and easy to manufacture. Preferably, the muffler cap 12 and the muffler core 14 are made of a substantially rigid material such as steel, aluminum, polyethylene, or polycarbonate. Moreover, the central blind bore 31 of the flange 30 may be alternatively configured for engaging a tool other than a hexagonal wrench, such as a screwdriver. Further, the flange 30 may include a protrusion having a plurality of flat sides rather than a blind bore. A noise muffler including such a protrusion may be tightened using tools such as pliers, an open-end wrench, a box wrench, or a socket wrench.

While the invention has been described with reference to preferred embodiments, it will be understood by those skilled in the art that various changes may be made and equivalents may be substituted for elements thereof without departing from the scope of the invention. In addition, many modifications may be made to adapt a particular situation or material to the teachings of the invention without departing from the scope of the invention.

Therefore, it is intended that the invention not be limited to the particular embodiments disclosed as the best mode contemplated for carrying out this invention, but that the invention will include all embodiments falling within the scope and spirit of the appended claims.

What is claimed is:

1. A noise muffler for a gas handling apparatus, comprising:
   a core with two ends and defining a central blind bore extending in an axial direction and having an inlet at one core end to receive waste gases into the blind bore in the axial direction and a plurality of radial bores between the core ends to redirect the waste gases to flow from the blind bore through the radial bores in directions substantially lateral to axial direction;
   a filter surrounding the core for filtering the waste gases, the filter having a side and two ends;
   a cap having a side wall covering the filter side and an end wall covering at least one end of the filter;
   the core further comprising an integral flange at the other core end to cover the other filter end; and
   means for defining multiple outlets for discharging the waste gases, the outlet defining means causing the waste gases flowing through the radial bores first to flow in directions lateral to the axial direction, then to flow through the filter in the axial direction and then be redirected again to exit the muffler indirections substantially lateral to the axial direction.

2. The noise muffler for of claim 1 wherein the core and the cap side wall are substantially cylindrical.

3. The noise muffler of claim 2 wherein said filter comprises woven polymer fibers.

4. The noise muffler of claim 1 wherein said flange is substantially circular and said filter is substantially cylindrical and abuts against said flange.

5. The noise muffler of claim 1 wherein said cap side wall is substantially cylindrical and one of said cap and flange comprises a plurality of clips opposite to the covered end of said cap to retain the cap on the core by engagement of the clips with the other of said cap and flange.

6. A noise muffler according to claim 1 wherein the core and the cap are cylindrical in shape and the filter substantially fills the interior of the cap between the cap side wall and the core.

7. A noise muffler according to claim 1 wherein the cap and flange are interconnected to prevent the waste gases from exiting other then by the outlet defining means.

8. A noise muffler according to claim 6 wherein the outlet defining means a plurality of slots in the side wall of the cap, the slots being displaced both radially from the direction of flow of the waste gases through the core openings and axially from the radial bores.

9. A noise muffler for use with a gas handling apparatus, comprising:
   a core with two ends and having a central piece defining a central blind bore extending in an axial direction with an inlet at one end to receive waste gases into the blind bore in the axial direction and a plurality of radial bores between the ends to redirect the waste gases to flow from the blind bore through the radial bores in directions substantially lateral to the axial direction, the one core end having means for attaching the muffler to the apparatus and the other core end comprising a flange and tool receiving means for enabling attachment of the muffler to the apparatus;
   a filter surrounding the central of filtering the waste gases, the filter having a side and two ends with one of the filter ends covered by the core flange; and
   a cap having an end wall covering the other filter end and a side wall covering the side of the filter and the core central piece, the cap side wall defining a plurality of outlets displaced radially from the directions in which the waste gases pass through the core openings;
   the cap end wall defining a hole through which the one core end is slidably passed, and the core flange and cap side wall comprising interconnecting means for releaseably affixing the flange and the cap side wall together and enclosing the filter by which to cause the waste gases flowing through the radial bores to be redirected to flow axially through the filter and then to exit the muffler only through the outlets in a direction substantially lateral to axial direction.

10. The noise muffler of claim 9 wherein the flange is substantially circular and the cap and the filter are substantially cylindrical in shape.

11. The noise muffler of claim 9 wherein the outlets are positioned in the cap side wall adjacent to the flange.

12. The noise muffler of claiem 11 wherein the radial bores are positioned to direct the waste gases in multiple radial directions and the outlet are positioned radially midway between the radial directions of the radial bores.

13. The noise muffler of claim 9 wherein the radial bores are positioned to direct the waste gases in multiple radial directions and the outlets are positioned radially midway between the radial directions of the radial bores.

* * * * *